United States Patent [19]
Weber et al.

[11] Patent Number: 5,422,476
[45] Date of Patent: Jun. 6, 1995

[54] GLASS CONTAINER INSPECTION MACHINE

[75] Inventors: Gary C. Weber; Timothy W. Shay; Mark P. Claypool, all of Horseheads, N.Y.

[73] Assignee: Emhart Glass Machinery Investments Inc., Wilmington, Del.

[21] Appl. No.: 121,796

[22] Filed: Sep. 15, 1993

[51] Int. Cl.⁶ .............................................. G01N 9/04
[52] U.S. Cl. .............................. 250/223 B; 250/224; 209/524
[58] Field of Search ..................... 209/524, 526, 529; 250/223 B, 224; 356/240

[56] References Cited

U.S. PATENT DOCUMENTS

| | | | |
|---|---|---|---|
| 4,020,949 | 5/1977 | Erdman | 356/240 |
| 4,731,649 | 3/1988 | Chang et al. | 356/240 |
| 4,914,289 | 4/1990 | Nguyen et al. | 250/223 B |

Primary Examiner—William L. Sikes
Assistant Examiner—James A. Dudek
Attorney, Agent, or Firm—Spencer T. Smith

[57] ABSTRACT

A machine for inspecting a container has an inspection conveyor for gripping and conveying containers delivered thereto at one speed. A feed conveyor delivers containers to the inspection conveyor at a slower speed. A container sensed on the inspection conveyor is brought to a stop at a selected location so that an inspection can take place.

11 Claims, 5 Drawing Sheets

GLASS CONTAINER INSPECTION MACHINE

Glass bottles are conventionally formed in an individual section (I.S.) machine. The formed bottles are then placed on a conveyor for routing through a number of inspection stations where they will be stopped so that an inspection can be performed.

Non round bottles pose special problems since they are difficult to spin about the axis of the finish (the threaded opening) and relative rotation between the finish and a check detector about this axis is conventionally required to find checks (a closed crack where the neck of the bottle joins the shoulder or on the finish or inside the finish). For example, Hungarian Patent No. 201,154 discloses a check detector wherein a non round bottle to be inspected is stopped at an inspection station by a Geneva mechanism which elevates the stopped bottle into a rotating check inspection head.

It is conventional to hold a round bottle at the inspection station while rotating it about its vertical axis so that an inspection operation can be conducted. U.S. Pat. Nos. 3,901,381 and 4,865,447 disclose such an inspection station where the finish of a spinning bottle is inspected for checks and the like and U.S. Pat. No. 5,028,769 discloses such an inspection station where the mold code located on the heel of the spinning bottle is inspected (read).

It is an object of the present invention to provide an improved glass container inspection machine which delivers a bottle to an inspection station and momentarily stops the bottle so that an inspection can take place.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings.

Figure 4:
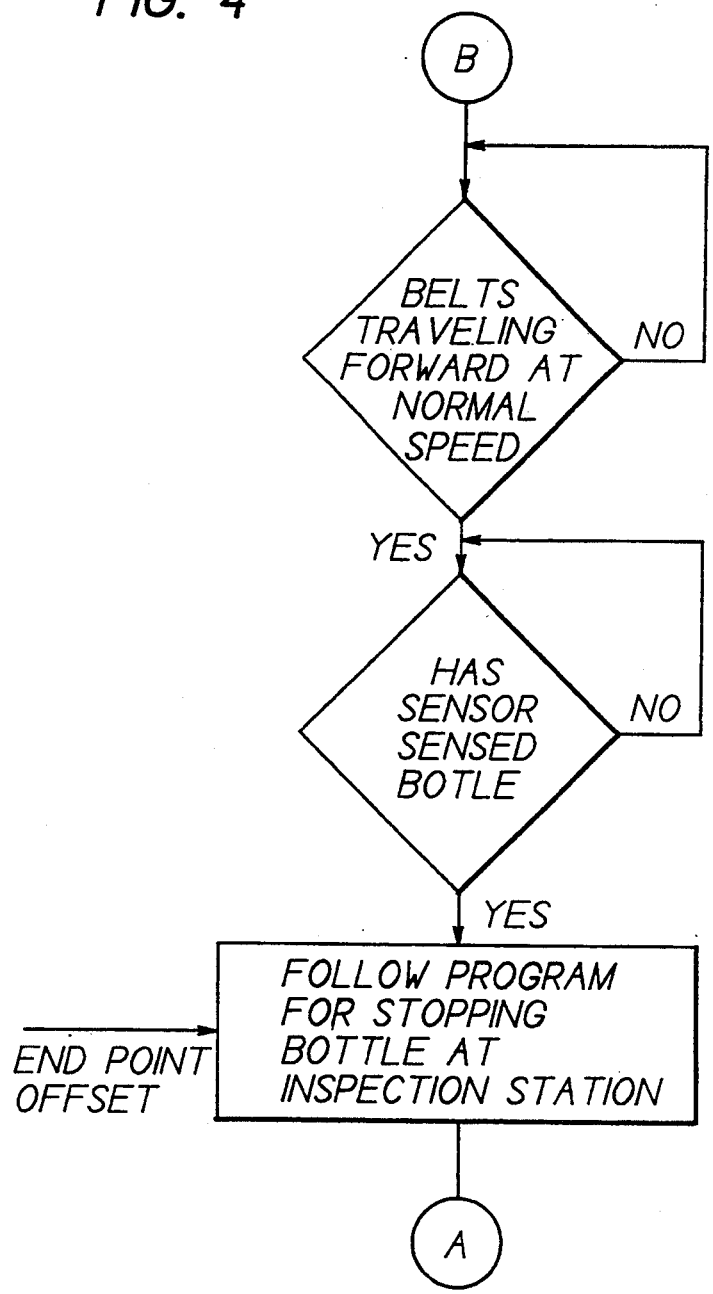
Figure 5:
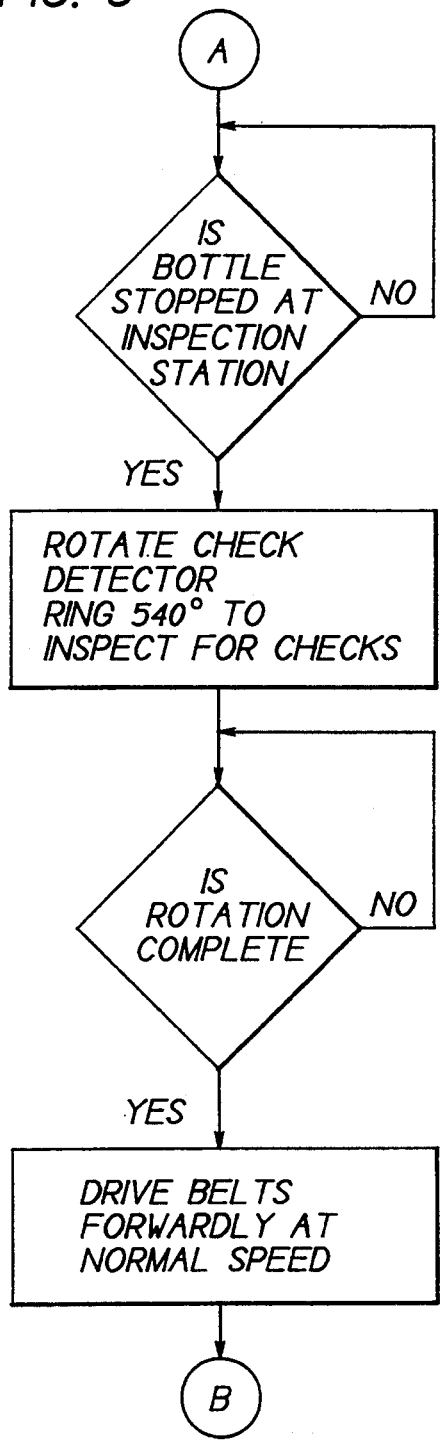
Figure 6:
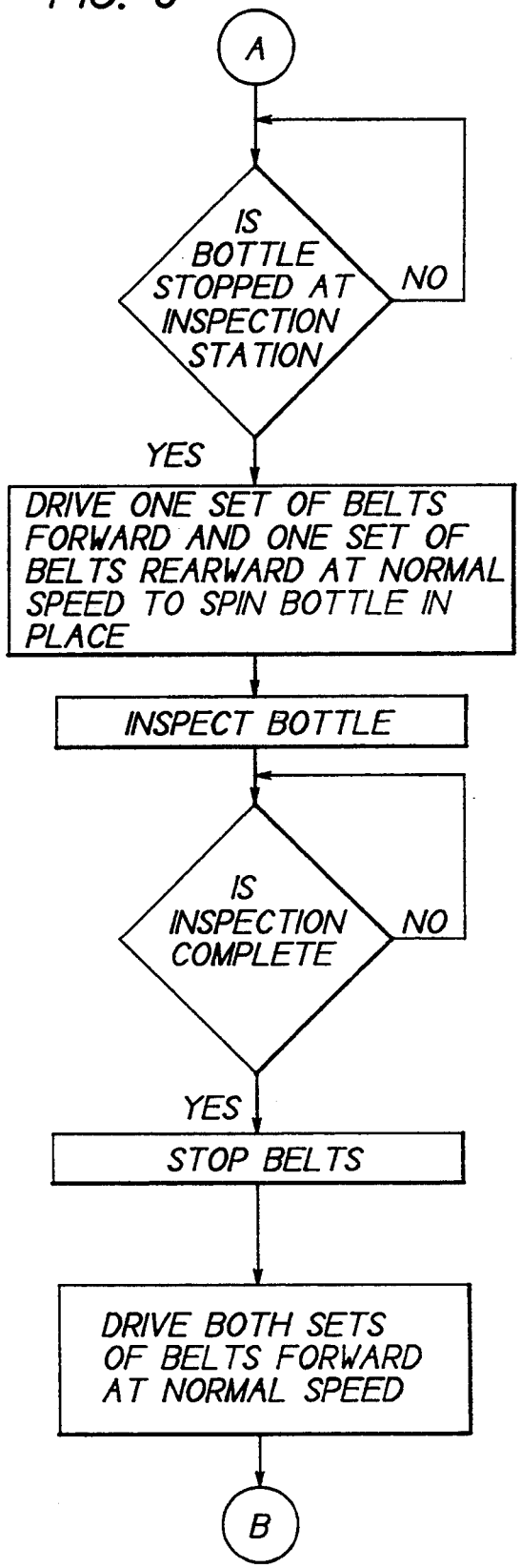

FIG. 4 is a first flow chart illustrating the operation of the controller for the servo motors driving the belt assemblies; and FIG. 5 is a second flow chart illustrating the operation of the inspection devices when the bottle is stopped at the inspection station and a non rotating bottle is to be inspected by rotating optics; and FIG. 6 is a third flow chart illustrating the operation of the controller for the servo motors driving the belt assemblies when spinning round bottles are to be inspected.

Spaced non round bottles 10, which may be made in an I.S. machine, are carried by a horizontal feed conveyor 12 which is moving at a constant speed S1 and are delivered to a second conveyor which is made up of opposed mirror image belt assemblies 14 each supporting a pair of continuous timing belts 16. These belts may have a compliant outer layer such as foam neoprene ®.

The belts on one side of the bottle path are driven clockwise at a higher constant speed S2 by one profiled motion actuator 18 such as a servo motor and the belts on the other side are driven counterclockwise at this second constant speed S2 by a second servo motor 18. The surface speed S2 of these opposed belts is substantially faster than the speed S1 of the conveyor 12 (approximately twice the speed of the feed conveyor). As a result, as soon as a bottle is gripped by these belts, its linear velocity changes from S1 to S2. Sensor 20 senses a bottle which is being carried by the belts 16 toward an inspection station.

Figure 2:
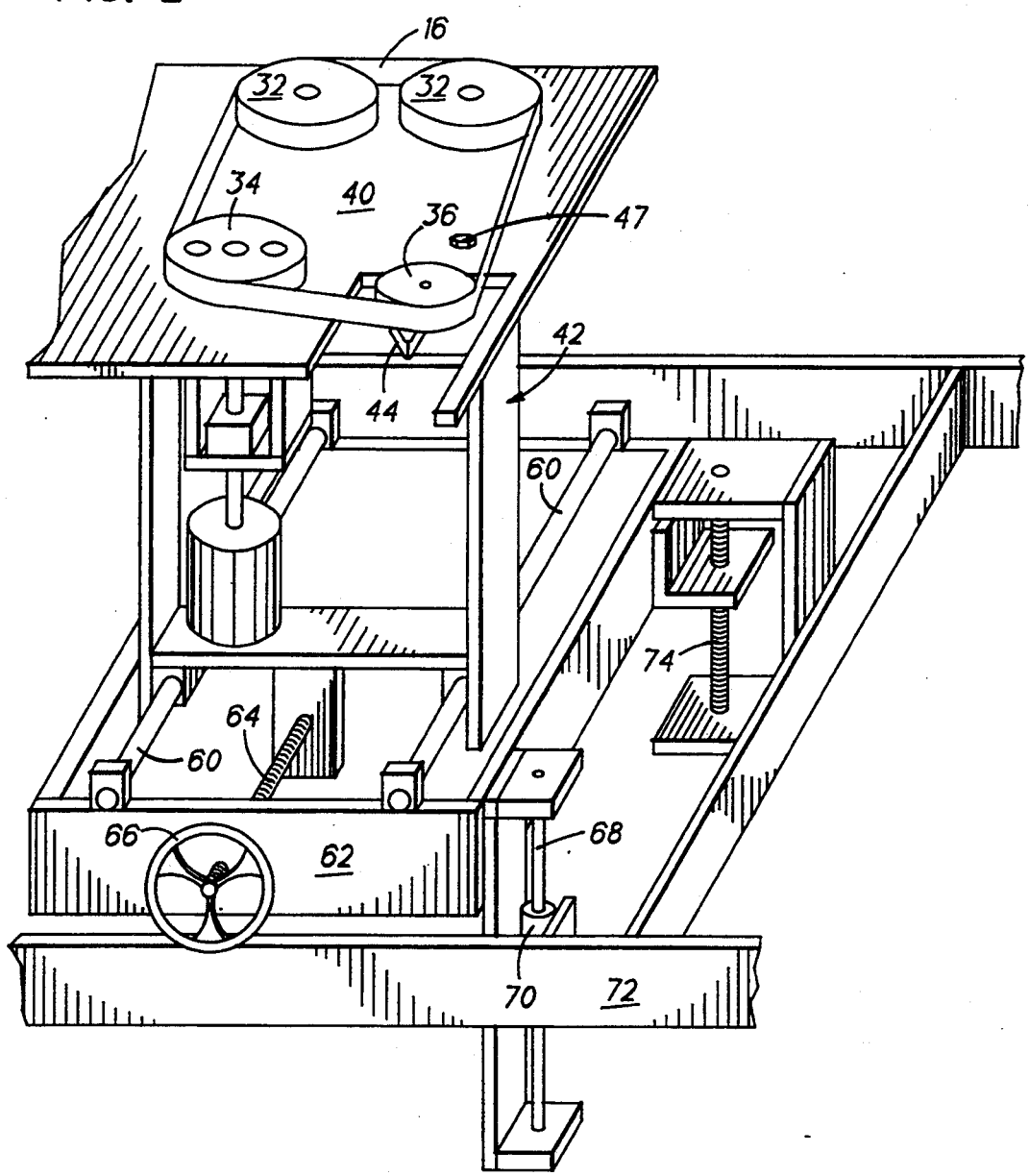
FIG. 2 is an oblique view of the machine illustrating how the lower belt of each belt assembly is supported.
Figure 3:
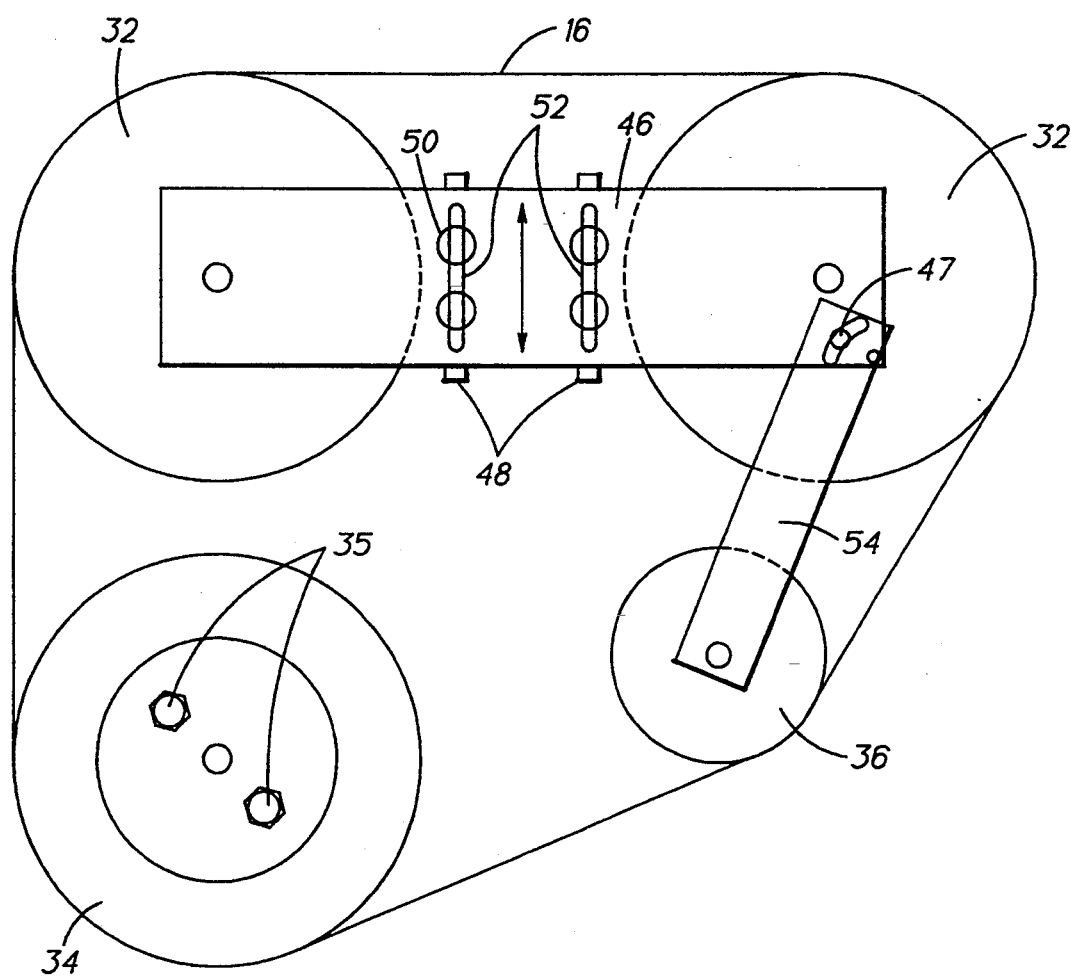
FIG. 3 is a top view showing how the upper belt of each belt assembly, is supported.

Each belt 16 is supported by a pair of front idlers 32, a drive roller 34 and an adjustable rear idler 36. The lower pair of front idlers 32 and the lower drive roller 34 of each belt assembly are mounted on the support plate 40 (FIG. 2) of a slide member 42. The rear idler 36 of each lower belt assembly is mounted on a bracket 44 which is pivotally secured to the support plate 40 and held in the desired position by a suitable fastener. The upper pair of front idlers 32 (FIG. 3) of each belt assembly are mounted on an upper support plate 46 which is secured to upstanding posts 48 with bolts 50 that extend through elongated slots 52 so that the upper support plate, and hence, the inner upper idler pair, can be transversely displaced towards or away from the conveyor path relative to the lower idler pair. This enables the second conveyor to grip and carry tapered containers whether round or non round. The posts 48 are secured to the support plate 40. The upper rear idler is mounted on the free end of a bracket 54 similar to the lower idler bracket 44 which can be pivotally displaced relative to the upper support plate 46 and secured thereto with a fastener 47 at a selected position. The upper drive roller 34 is secured to the lower drive roller by threaded bolts 35 so that the spacing therebetween can be changed as the spacing between the upper and lower front and rear idlers is changed by placing shims (not shown) between the posts and the upper support plate. Optionally, the upper 34 and lower 35 drive rollers could be one single drive roller which would permit vertical movement of one belt relative to the other belt.

Additionally, each belt assembly can be shifted as a whole towards or away from (transverse) the conveyor path since the belt assembly slide member 42 is mounted on a pair of guide rods 60 which extend between the front and rear walls of a box like housing 62. Transverse displacement is controlled via a feed screw 64 which ends at a turning wheel 66. Vertical guide rails 68 are also secured at each corner of the box like housing (only one is shown for purposes of clarity) and these vertical guide rails 68 are received by suitable sleeves 70 which are secured to the machine base 72. Vertical displacement of the box like frame and hence, the belt assembly is effected by rotatable threaded rods 74 which interconnect the four corners of the box like frame and the machine base (only one shown). These threaded rods can be linked together for displacement as pairs or all four can be interconnected.

As shown in FIG. 4, when the sensor senses the presence of a bottle which is travelling at the speed S2 of the second conveyor, the controller C which controls the operation of the two servo motors 18 driving the belt assemblies follows a predefined feed program which will decelerate the bottle and stop its forward displacement at the inspection station. Provision is made in the form of an end point offset to change the location where the bottle stops to the exact desired location during set-up.

Depending on whether the bottles being tested are round or non round, a separate spacing device may be required to assure that one bottle will not interfere with the inspection of the next forward bottle.

Figure 1:
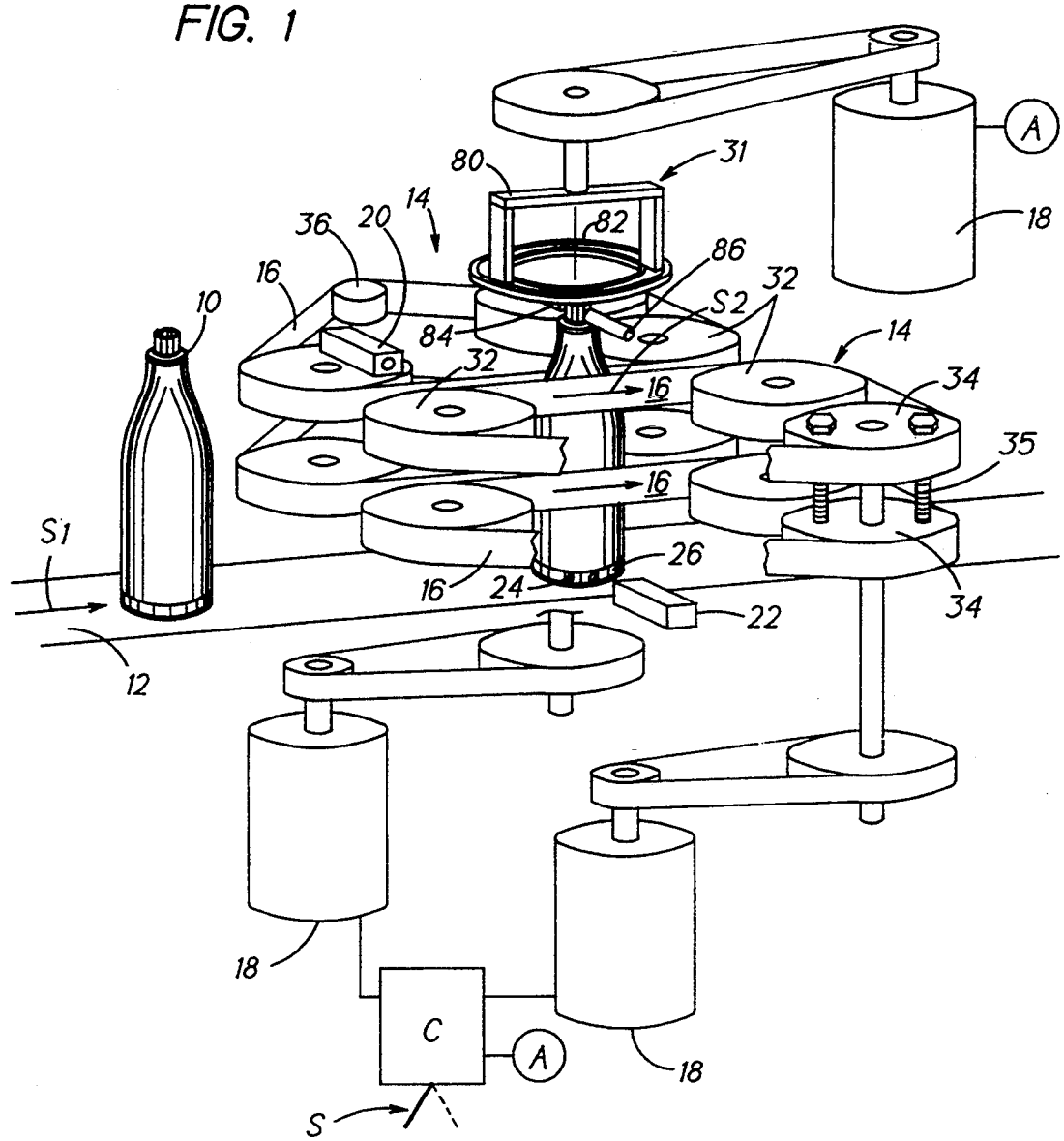
FIG. 1 is an oblique view of the container inspecting machine made in accordance with the teachings of the present invention.

The check detector 31 includes a bracket 80 to which is secured a check detector ring 82 on which a plurality of associated pairs of light sources 84 and sensors 86 can be mounted. In the preferred embodiment, high intensity-low degradation light sources such as Welch-Allyn halogen lamps and EG&G photo diode sensors are used. The sensors and light sources, as shown in FIG. 1, are mounted below the top of the container and are mounted to define a path when the check ring is stopped at the illustrated position or the 180° switched position, through which the top of the bottle can pass as it approaches or leaves the inspection station. The check detector bracket is mounted on a shaft which is rotatably driven by a servo motor 18 controlled by the controller C and signals can be routed via a slip ring connector, for example.

Another inspection device which might also inspect the non rotating bottle could be a plug gage and/or ring gage or a pressure testing device such as shown in U.S. Pat. No. 4,490,800.

As can be seen from FIG. 5, when the bottle is stopped at the inspection station, the check inspection device is operated to inspect the non rotating bottle. The check detector ring, by rotating 540°, will completely scan the top of the bottle and stop at one of the two acceptable orientations (the optics can be arranged as shown to define two 180° paths through it, for example, or the check detector ring could have other than 180° related stopped positions). When the inspection is completed, the drive belts will again be conjointly driven forward at their normal speed to remove the inspected bottle from the inspection station.

To change the operating mode of the machine, the operator need only switch the machine from the first mode where the bottle is not rotated to the second mode where the bottle will be rotated at the inspection station. The switch, which is schematically shown as S in FIG. 1, could be a mechanically operated switch or it could be a program entry into the control.

Referring to FIG. 6, when the bottle is stopped at the inspection station, one set of the belts will be driven rearward at S2 and the other set will be conjointly driven forward at S2 so that the bottle will spin in place at the inspection location. During spinning, inspection (check detection or mold number reading, for example) takes place. Following inspection, the belts are stopped and then both sets are driven again at speed S2 in the forward direction to carry the bottles forwardly for deposit on the same feed conveyor or a different removal conveyor.

The optical inspection can be completed with stationary optical sensors 86 or with the check inspection head rotating in an opposite direction to speed the inspection process. A mold number reader 22 will also read the molded code 24 on the heel 26 of the spinning bottle.

We claim:

1. A machine for inspecting a vertically standing container at a selected inspection station comprising
   an inspection conveyor including a pair of belt conveyors having spaced opposed parallel portions for gripping and conveying containers delivered thereto forwardly to the inspection location,
   means for driving said belt conveyors forwardly at a selected speed,
   a feed conveyor for delivering containers to said inspection conveyor at a second slower speed,
   means for sensing when a container being conveyed by said inspection conveyor at said selected speed, is at a selected location,
   means for bringing a sensed container to a stop at the selected inspection station, and
   means for inspecting the stopped container.

2. A machine for inspecting a container according to claim 1, wherein said inspection means comprises a check detector.

3. A machine for inspecting a container according to claim 2, wherein said check detector comprises
   a rotatable check detector ring including at least one inspection device extending downwardly below the top of a container to be inspected,
   means for stopping the rotation of said check detector ring at at least one selected orientation whereat a path exists for a container to be conveyed to and from said inspection station by said inspection conveyor without striking one inspection device, and
   means for rotating said check detector ring and stopping said check detector ring at said selected orientation, while a container is stopped at said inspection station, so that an inspection for a check can be completed.

4. A machine for inspecting a container according to claim 3, further comprising
   means for driving said belt conveyors forwardly at said selected speed to remove the inspected container from said inspection station.

5. A machine for inspecting a cylindrical container comprising
   an inspection conveyor including a pair of belt conveyors having spaced opposed parallel portions for gripping and conveying containers delivered thereto,
   means for driving said belt conveyors forwardly at a selected speed,
   a feed conveyor for delivering containers to said inspection conveyor at a second slower speed,
   means for sensing when a container, being conveyed by said inspection conveyor, is at a selected location,
   means for bringing a sensed container to a stop at a selected inspection location,
   means for rotating a stopped container about its axis including
      means for driving one of said belt conveyors forwardly at a predetermined speed, and
      means for conjointly driving the other one of said belt conveyors rearwardly at said predetermined speed, and
   means for inspecting the rotating container.

6. A machine for inspecting a cylindrical container according to claim 5, wherein said inspection means comprises a mold number reader.

7. A machine for inspecting a cylindrical container according to claim 5, wherein said inspection means comprises a check detector.

8. A machine for inspecting a cylindrical container according to claim 5, further comprising
   means for stopping said pair of belt conveyors after inspection has been completed and
   means for driving said belt conveyors forwardly at said selected speed to remove the inspected container from said inspection station.

9. A machine for inspecting a cylindrical container according to claim 5, wherein each of said belt conveyors comprises upper and lower belts.

10. A machine for inspecting a container located at an inspection station comprising
an inspection conveyor for conveying vertical containers to the inspection station,
a check detector at the inspection station including
a horizontally disposed rotatable check detector ring,
at least one inspection device mounted on said check detector ring to extend downwardly below the top of a container to be inspected,
means for stopping the rotation of said check detector ring at at least one selected orientation whereat a path exists for a container to be conveyed to and from the inspection station by said conveyor without striking said at least one inspection device,
means for rotating said check detector ring and stopping said check detector ring at said selected orientation while a container is stopped at the inspection station, so that an inspection can be completed.

11. A machine according to claim 10 wherein said inspection device includes a light source and an associated sensor.

* * * * *